US011730394B2

(12) United States Patent
Kang et al.

(10) Patent No.: US 11,730,394 B2
(45) Date of Patent: Aug. 22, 2023

(54) SYSTEM AND METHOD FOR CALIBRATING RATIO OF BODY SIZE OF SUBJECT

(71) Applicant: KOREA INSTITUTE OF SCIENCE AND TECHNOLOGY, Seoul (KR)

(72) Inventors: Donghoon Kang, Seoul (KR); Jinwook Kim, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 387 days.

(21) Appl. No.: 17/103,091

(22) Filed: Nov. 24, 2020

(65) Prior Publication Data
US 2022/0110543 A1    Apr. 14, 2022

(30) Foreign Application Priority Data

Oct. 12, 2020 (KR) .................. 10-2020-0131096

(51) Int. Cl.
| | |
|---|---|
| *G01P 13/00* | (2006.01) |
| *A61B 5/107* | (2006.01) |
| *G01B 21/00* | (2006.01) |
| *A61B 5/11* | (2006.01) |
| *A61B 5/00* | (2006.01) |
| *G16H 10/60* | (2018.01) |
| *G16H 50/30* | (2018.01) |

(52) U.S. Cl.
CPC .......... *A61B 5/1072* (2013.01); *A61B 5/1114* (2013.01); *A61B 5/1116* (2013.01); *A61B 5/1121* (2013.01); *A61B 5/7225* (2013.01); *A61B 5/7278* (2013.01); *G01B 21/00* (2013.01); *G01P 13/00* (2013.01); *G16H 10/60* (2018.01); *G16H 50/30* (2018.01); *A61B 2560/0223* (2013.01)

(58) Field of Classification Search
CPC ... A61B 5/1072; A61B 5/1114; A61B 5/1116; A61B 5/1121; A61B 5/7225; A61B 5/7278; A61B 2560/0223; G16H 10/60; G16H 50/30; G01B 21/00; G01P 13/00
See application file for complete search history.

(56) References Cited

FOREIGN PATENT DOCUMENTS

| | | | |
|---|---|---|---|
| JP | 6288858 B2 | 3/2018 | |
| JP | 2020146103 A * | 9/2020 | ............... A61B 5/11 |
| JP | 2020146103 A | 9/2020 | |
| KR | 1020100002803 A | 1/2010 | |

(Continued)

*Primary Examiner* — Kyle R Quigley
*Assistant Examiner* — Xiuqin Sin
(74) *Attorney, Agent, or Firm* — Rabin & Berdo, P.C.

(57) ABSTRACT

Embodiments relate to a system and method for calibrating a ratio of body size of a subject including setting a body coordinate system of each body segment of the subject, calculating a first rotation matrix from a world coordinate system set based on the ground to a sensor coordinate system of each motion sensor when the subject takes a first basic pose, calculating a second rotation matrix from the world coordinate system to the sensor coordinate system of each motion sensor when the subject takes a second basic pose, calculating a third rotation matrix from the world coordinate system to the body coordinate system of a trunk for a first motion sensor attached to the trunk of the subject, and calculating a ratio of body size of the subject based on the third rotation matrix.

12 Claims, 13 Drawing Sheets

(56) References Cited

FOREIGN PATENT DOCUMENTS

| KR | 1020130060441 A | 6/2013 |
|----|-----------------|--------|
| KR | 101282953 B1    | 7/2013 |
| KR | 101869164 B1    | 6/2018 |
| KR | 102018951 B1    | 9/2019 |
| KR | 1020200066971 A | 6/2020 |

* cited by examiner

Upper body

Lower body

Full body

SYSTEM AND METHOD FOR CALIBRATING RATIO OF BODY SIZE OF SUBJECT

CROSS-REFERENCE TO RELATED APPLICATION

This application claims priority to Korean Patent Application No. 10-2020-0131096, filed on Oct. 12, 2020, and all the benefits accruing therefrom under 35 U.S.C. § 119, the contents of which in its entirety are herein incorporated by reference.

Technical Field

Embodiments of the present disclosure relate to motion capture technology using motion sensors, and more particularly, to a system and method for self-calibration of a ratio of body size including a ratio of size of the body segment having a motion sensor attached thereto, a ratio of the upper body, a ratio of the lower body and/or a ratio of the full body, using sensor data of the motion sensor.

Background Art

Motion capture technology is technology that tracks human movements, and can be used in various fields such as film making or animation creation, sport movement analysis and rehabilitation medicine.

For accurate motion capture, it is necessary to measure the body size of a target subject for motion capture. In particular, ratios of body segments to the full body largely affect the motion capture accuracy.

Currently, a leading motion capture system in the motion capture field is Xsens MVN. The MVN has a simple system architecture implemented by a microelectromechanical system (MEMS) inertial measurement unit (IMU) sensor-based motion capture dedicated suit and a data processing device (for example, a computer) without a separate camera, and is used in a wide range of applications.

FIG. 1 is a diagram for describing a process of acquiring a ratio of body size using the existing MVN product.

However, the MVN product needs to acquire a ratio of body size including a ratio of the upper body to the full body, a ratio of the lower body to the full body, and a ratio of the size from the end of one arm to the end of the other arm when stretching out both arms (for example, as shown in FIG. 1) by directly measuring and inputting the corresponding body segment using a separate external device such as a ruler or a camera.

DISCLOSURE

Technical Problem

According to an aspect of the present disclosure, there is a system for self-calibration of a ratio of body size including a ratio of size of the body segment having an inertial sensor attached thereto, a ratio of the upper body, a ratio of the lower body and/or a ratio of the full body using sensor data of the motion sensor.

In addition, there is a method for calibrating a ratio of body size of a subject and a computer readable recording medium having the same recorded thereon.

Technical Solution

A method for calibrating a ratio of body size of a subject, performed by a processor, according to an aspect of the present disclosure may include setting a body coordinate system of each body segment in a subject having a plurality of motion sensors attached to a plurality of body segments, calculating a first rotation matrix from a world coordinate system set based on the ground to a sensor coordinate system of each motion sensor when the subject takes a first basic pose, calculating a second rotation matrix from the world coordinate system to the sensor coordinate system of each motion sensor when the subject takes a second basic pose, calculating a third rotation matrix from the world coordinate system to the body coordinate system of a trunk having a first motion sensor attached thereto for the first motion sensor attached to the trunk of the subject, and calculating a ratio of body size of the subject based on the outputs of the plurality of motion sensors and the third rotation matrix.

In an embodiment, the first basic pose may be a pose in which an arm or a leg of the subject is positioned toward the ground, and the second basic pose may be a pose in which at least one of the arm or the leg is moved to a side from the first basic pose.

In an embodiment, calculating the third rotation matrix from the world coordinate system to the body coordinate system of the trunk having the first motion sensor attached thereto for the first motion sensor attached to the trunk of the subject may include setting a first unit vector based on a direction of gravity, setting a second unit vector based on the first and second rotation matrices, setting a third unit vector based on the first and second unit vectors, and acquiring the third rotation matrix from the world coordinate system to the body coordinate system of the trunk having the first motion sensor attached thereto. Here, the third rotation matrix is given as the following Equation 1.

$$A \triangleq [v_1 \ v_2 \ v_3] \quad \text{[Equation 1]}$$

In an embodiment, the second unit vector is represented by the following Equation 2.

$$v_2 \triangleq e/\|e\| \quad \text{[Equation 2]}$$

Here, v2 is the second unit vector, and e is represented by the following Equation 3.

$$e \triangleq (a_1, a_2, a_3) \quad \text{[Equation 3]}$$

Here, a1, a2, a3 are calculated by the following Equation 4.

$$E - E^T \triangleq \begin{bmatrix} 0 & -a_3 & a_2 \\ a_3 & 0 & -a_1 \\ -a_2 & a_1 & 0 \end{bmatrix} \quad \text{[Equation 4]}$$

Here, E denotes an average matrix of $N_k^{-1} T_k$ (where k=2, ..., n), $N_k$ denotes the first rotation matrix, $T_k$ denotes the second rotation matrix, and n denotes the number of the remaining motion sensors except the first motion sensor attached to the trunk among the plurality of motion sensors.

In an embodiment, calculating the ratio of body size of the subject may include acquiring the outputs of the plurality of motion sensors while the subject is moving arbitrarily, setting a motion unit vector for each of the plurality of motion sensors, and calculating a ratio of at least some of the plurality of body segments in a motion pose taken by the subject based on the motion unit vector.

In an embodiment, the motion unit vector of the first motion sensor attached to the trunk among the plurality of motion sensors may be set in a horizontal direction of the trunk, and the motion unit vector of the remaining motion sensors in the plurality of motion sensors may be set by the following Equation 5.

$$c_k^i \triangleq -R_k^i v_1 (k = 2, \ldots, n) \qquad \text{[Equation 5]}$$

Here, ck denotes the motion unit vector of $k^{th}$ motion sensor, i denotes a sensing timestamp, and v1 denotes the first unit vector set based on the direction of gravity. Additionally, $R_k$ is represented by the following Equation 6.

$$R_k^i \triangleq A^{-1} U_k^i \qquad \text{[Equation 6]}$$

Here, A denotes the third rotation matrix, and $U_k$ denotes the output of the corresponding motion sensor.

In an embodiment, calculating the ratio of at least some of the plurality of body segments in the motion pose taken by the subject based on the motion unit vector may include calculating a ratio of sizes of body segments that form a first closed loop. The body segments that form the first closed loop include the trunk and both arms, and the ratio of the sizes of the body segments that form the first closed loop is calculated by the following Equation 7.

$$\min_{x \in \mathbb{R}^5} \sum_{i=1}^{m} \|F_i x\|^2 \qquad \text{[Equation 7]}$$

where, $x = (x_1, \ldots, x_5) \in \mathbb{R}^5$ and $\|x\| = 1$ $$F_i \triangleq [\, c_1^i \quad c_2^i \quad c_3^i \quad -c_4^i \quad -c_5^i \,] \in \mathbb{R}^{3 \times 5}$$

Here, x is a set of ratios of the body segments that form the first closed loop, and m is a time range in which the outputs of the plurality of motion sensors are acquired.

In an embodiment, when the first closed loop is symmetrical, the ratio of the sizes of the body segments that form the first closed loop is calculated by the following Equation 8.

$$\min_{x \in \mathbb{R}^3} \sum_{i=1}^{m} \|G_i x\|^2 \qquad \text{[Equation 8]}$$

where, $x = (x_1, \ldots, x_3) \in \mathbb{R}^5$ and $\|x\| = 1$ $$G_i \triangleq [\, c_1^i \quad (c_2^i - c_5^i) \quad (c_3^i - c_4^i) \,] \in \mathbb{R}^{3 \times 3}$$

Here, the symmetrical first closed loop is such that a second body segment having the second motion sensor attached thereto and a fifth body segment having the fifth motion sensor attached thereto are symmetrical, and a third body segment having the third motion sensor attached thereto and a fourth body segment having the fourth motion sensor attached thereto are symmetrical.

In an embodiment, calculating the ratio of at least some of the plurality of body segments in the motion pose taken by the subject based on the motion unit vector may include calculating a ratio of sizes of body segments that form a second closed loop. The body segments that form the second closed loop include the trunk and both legs, and the ratio of the sizes of the body segments that form the second closed loop is calculated by the following Equation 9.

$$\min_{x \in \mathbb{R}^6} \sum_{i=1}^{m} \|H_i x\|^2 \qquad \text{[Equation 9]}$$

where, $x = (x_1, \ldots, x_6) \in \mathbb{R}^6$ and $\|x\| = 1$ $$H_i \triangleq [\, c_1^i \quad c_6^i \quad c_7^i \quad v_2 \quad -c_8^i \quad -c_9^i \,] \in \mathbb{R}^{3 \times 6}$$

Here, x is a set of ratios of the body segments that form the second closed loop, and m is a time range in which the outputs of the plurality of motion sensors are acquired.

In an embodiment, calculating the ratio of at least some of the plurality of body segments in the motion pose taken by the subject based on the motion unit vector may include calculating a ratio of sizes of body segments that form a third closed loop. The body segments that form the third closed loop include one arm and the trunk, the calculated ratio of the size of the trunk indicates a ratio of a vertical length of the trunk, and the ratio of the sizes of the body segments that form the third closed loop is calculated by the following Equation 10.

$$\min_{x \in \mathbb{R}^3} \sum_{i=1}^{m} \|I_i x\|^2 \qquad \text{[Equation 10]}$$

where, $x = (x_1, \ldots, x_3) \in \mathbb{R}^3$ and $\|x\| = 1$ $$I_i \triangleq [\, c_2^i \quad c_3^i \quad -h^i \,] \in \mathbb{R}^{3 \times 3}$$

Here, x is a set of ratios of the body segments that form the third closed loop, and m is a time range in which the outputs of the plurality of motion sensors are acquired.

In an embodiment, calculating the ratio of at least some of the plurality of body segments in the motion pose taken by the subject based on the motion unit vector may include calculating a ratio of sizes of body segments that form a fourth closed loop. Here, the body segments that form the fourth closed loop include one arm, the trunk and one thigh, the calculated ratio of the size of the trunk indicates a ratio of a vertical length of the trunk, and the ratio of the sizes of the body segments that form the fourth closed loop is calculated by the following Equation 11.

$$\min_{x \in \mathbb{R}^4} \sum_{i=1}^{m} \|J_i x\|^2 \qquad \text{[Equation 11]}$$

where, $x = (x_1, \ldots, x_4) \in \mathbb{R}^4$ and $\|x\| = 1$ $$J_i \triangleq [\, c_2^i \quad c_3^i \quad -c_6^i \quad -h^i \,] \in \mathbb{R}^{3 \times 4}$$

Here, x is a set of ratios of the body segments that form the fourth closed loop, and m is a time range in which the outputs of the plurality of motion sensors are acquired.

A computer-readable recording medium according to another aspect of the present disclosure may store program instructions that can be read by a computing device and executed by the computing device. Here, when the program instructions are executed by a processor of the computing device, the program instructions perform the method according to the above-described embodiments.

A system for calibrating a ratio of body size of a subject according to still another aspect of the present disclosure includes a plurality of motion sensors attached to a plurality of body segments of the subject, and a data processing device to acquire outputs of the plurality of motion sensors and calibrate a ratio of body size of the subject. The data processing device may include setting a body coordinate system of each body segment in the subject, calculating a first rotation matrix from a world coordinate system set based on the ground to a sensor coordinate system of each motion sensor when the subject takes a first basic pose, calculating a second rotation matrix from the world coordinate system to the sensor coordinate system of each motion sensor when the subject takes a second basic pose, calculating a third rotation matrix from the world coordinate system to the body coordinate system of a trunk having a first motion sensor attached thereto for the first motion sensor attached to the trunk of the subject, and calculating a ratio of body size of the subject based on the outputs of the plurality of motion sensors and the third rotation matrix.

Advantageous Effects

The system for calibrating a ratio of body size of a subject according to an embodiment of the present disclosure does not use a separate external device, for example, a rule or a camera to calculate ratios of various body sizes including a ratio of size of the body segment having a motion sensor attached thereto, a ratio of the upper body, a ratio of the lower body and/or a ratio of the full body. The system can achieve self-calibration by calculating the ratio of body size of the subject easily, conveniently and accurately using the motion sensor required for a motion capture system.

The effects of the present disclosure are not limited to the above-mentioned effects, and other effects not mentioned herein will be clearly understood by those skilled in the art from the appended claims.

DESCRIPTION OF DRAWINGS

The following is a brief introduction to necessary drawings in the description of the embodiments to describe the technical solutions of the embodiments of the present disclosure or the existing technology more clearly. It should be understood that the accompanying drawings are for the purpose of describing the embodiments of the present disclosure and not intended to be limiting of the present disclosure. Additionally, for clarity of description, the accompanying drawings may show some modified elements such as exaggerated and omitted elements.

BEST MODE

The terminology used herein is for the purpose of describing particular embodiments and not intended to be limiting of the present disclosure. Unless the context clearly indicates otherwise, the singular forms as used herein include the plural forms as well. The term "comprises" or "includes" when used in this specification, specifies the presence of stated features, regions, integers, steps, operations, elements, and/or components, but does not preclude the presence or addition of one or more other features, regions, integers, steps, operations, elements and/or components.

Unless otherwise defined, all terms (including technical and scientific terms) used herein have the same meaning as commonly understood by those skilled in the art. It is further understood that terms, such as those defined in commonly used dictionaries, should be interpreted as having a meaning that is consistent with their meaning in the context of the relevant art document, and will not be interpreted in an idealized or overly formal sense unless expressly so defined herein.

Hereinafter, the embodiments of the present disclosure will be described in detail with reference to the accompanying drawings.

A system for calibrating a ratio of body size of a subject (hereinafter, a calibration system) according to an aspect of the present includes a plurality of motion sensors and a data processing device. In specific embodiments, the calibration system may be used as a system for automatically calibrating a ratio of body size of the subject in a motion capture system for capturing the motion of the subject. In this case, the operation of calibrating a ratio of body size is performed before the motion capture operation to accurately capture the motion of the subject.

The calibration system 1 according to embodiments may have aspects of entirely hardware, entirely software, or partly hardware and partly software. For example, the system may refer collectively to hardware capable of processing data and software that manages the hardware. The term "unit", "module", "device" or "system" as used herein is intended to refer to a combination of hardware and software that runs by the corresponding hardware. For example, the hardware may be a data processing device including a Central Processing Unit (CPU), a Graphic Processing Unit (GPU) or other processor. Additionally, the software may refer to a process being executed, an object, an executable, a thread of execution and a program.

The motion sensor is a sensor used for motion capture. In an embodiment, the motion sensor includes an inertial sensor. The inertial sensor may be, for example, an inertial measurement unit (IMU) sensor, but is not limited thereto.

The plurality of motion sensors is attached to a plurality of body segments of the target subject for motion capture.

Figure 1:
FIG. 1 is a diagram for describing a process of acquiring a ratio of body size using the existing MVN product.
Figure 2:
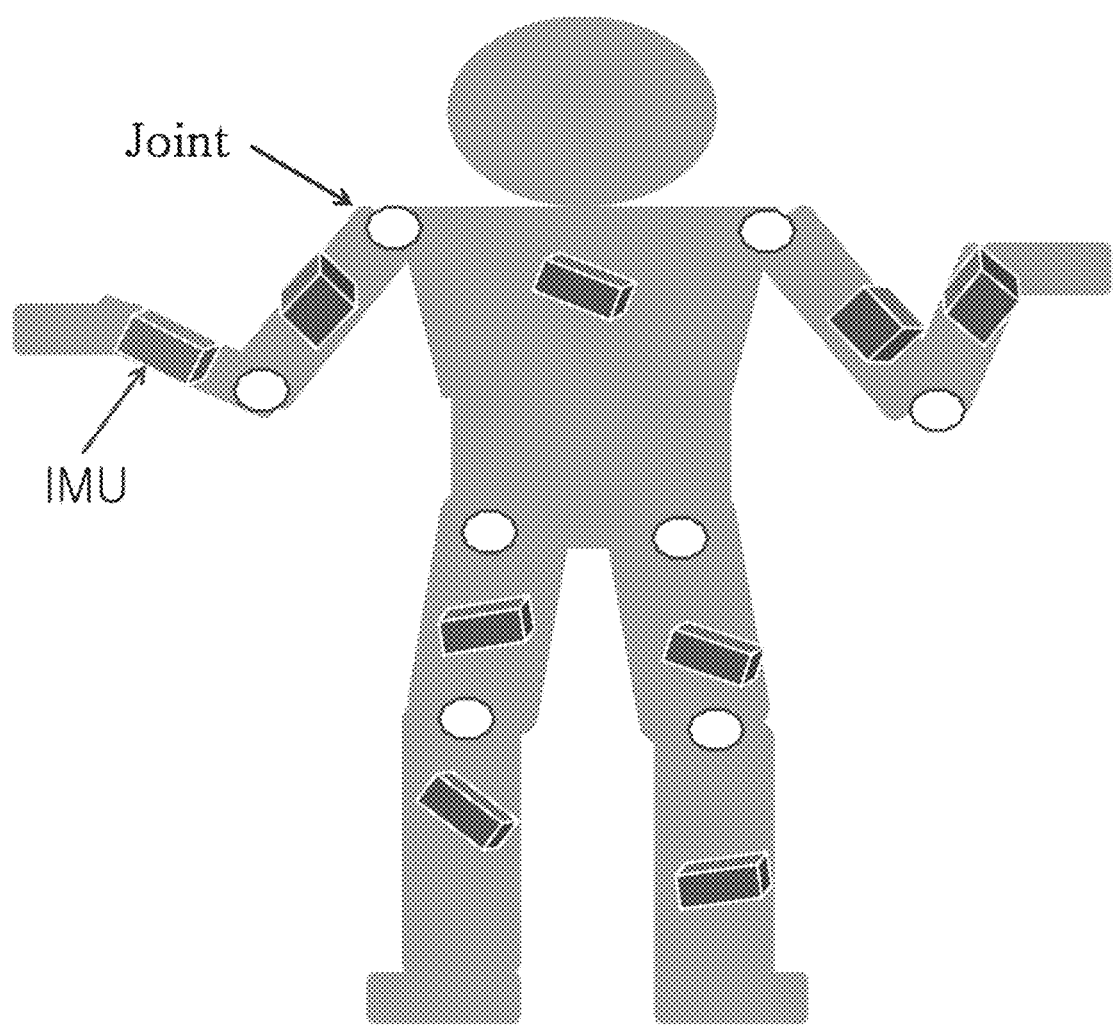
FIG. 2 is a diagram showing a subject having a plurality of motion sensors attached thereto according to an embodiment of the present disclosure.

FIG. 2 is a diagram showing the subject having the plurality of motion sensors attached thereto according to an embodiment of the present disclosure.

Referring to FIG. 2, a plurality of body segments includes the trunk of the subject. Additionally, the plurality of body segments includes body segments that are rotatable around a predetermined axis. The rotatable body segments include a body segment from the shoulder joint to the arm joint (referred to as "upper arm"), a body segment from the arm joint to the wrist joint (referred to as "lower arm"), a body segment from the hip joint to the knee joint (referred to as "thigh"), and a body segment from the knee joint to the ankle joint (referred to as "calf"). These body segments are configured to rotate around the connected joint axis.

As shown in FIG. 2, among the plurality of motion sensors, a first motion sensor may be attached to the trunk, and second to ninth motion sensors may be each attached to the above-described rotatable body segments on the left/right sides. For example, two motion sensors may be attached to each of the left arm and the right arm. Additionally, two motion sensors may be attached to each of the left leg and the right leg.

The motion sensor may be attached to the corresponding body segment in an arbitrary direction and/or at an arbitrary location.

The calibration system may perform a self-calibration operation of calculating a ratio of body size of the subject based on the outputs of the plurality of motion sensors attached as shown in FIG. 2 (for example, by the data processing device). The outputs of the plurality of motion sensors include sensor data for each motion sensor.

The calibration system may calculate a ratio of size of the body segment having the motion sensor attached thereto. For example, a ratio of rotatable body segment size, a ratio of thigh length, a ratio of calf length, a ratio of upper arm length, and/or a ratio of lower arm length may be calculated.

Additionally, the calibration system may calculate a ratio of upper body size, a ratio of lower body size and/or a ratio of full body size.

That is, the calibration system may calculate ratios of various body sizes including a ratio of rotatable body segment size, a ratio of upper body size, a ratio of lower body size and/or a ratio of full body size.

A method for calibrating a ratio of body size of a subject (hereinafter, "a calibration method") according to another aspect of the present disclosure is performed by a computing device including a processor. The computing device may be the data processing device of the calibration system, but is not limited thereto.

For clarity of description, the present disclosure will be described in more detail with regard to the embodiments in which the calibration method is applied to the subject having the plurality of motion sensors each attached to the trunk, the upper arms, the lower arms, the thighs and the calves on the left/right sides as shown in FIG. 2. However, those skilled in the art will clearly understand that the present disclosure is not limited to these embodiments.

Figure 3:
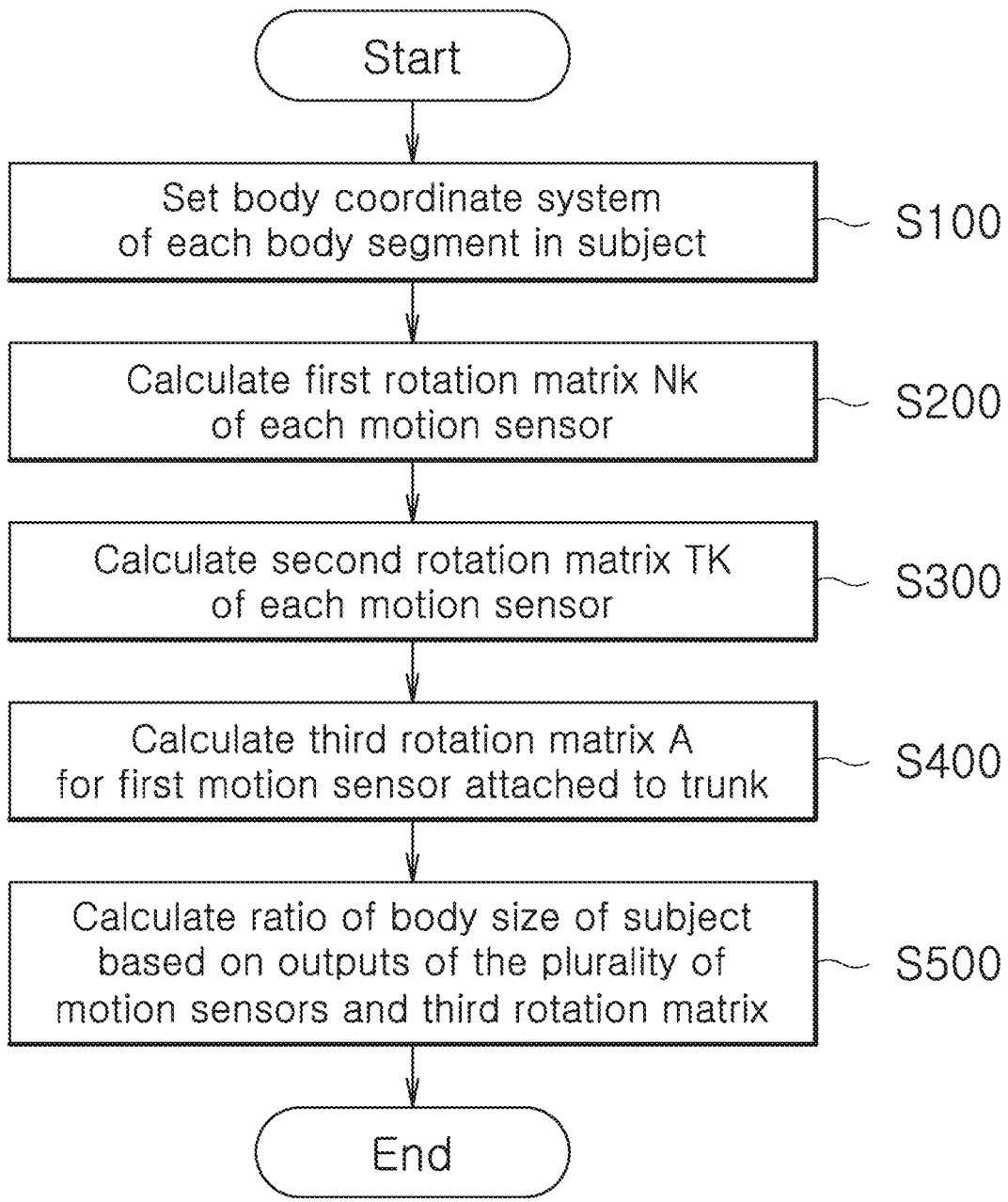
FIG. 3 is a flowchart of a method for calibrating a ratio of body size according to an embodiment of the present disclosure.

FIG. 3 is a flowchart of the method for calibrating a ratio of body size according to an embodiment of the present disclosure.

The embodiment of FIG. 3 uses various coordinate systems. For example, a world coordinate system {W} fixed to the ground and a body coordinate system {B} fixed to each body segment are used.

Referring to FIG. 3, the method for calibrating a ratio of body size (hereinafter, the calibration method) includes the step (S100) of setting the body coordinate system of each body segment of the subject having the plurality of motion sensors attached to the plurality of body segments. The body coordinate system is set for the body segment having the motion sensor attached thereto.

Figure 4:
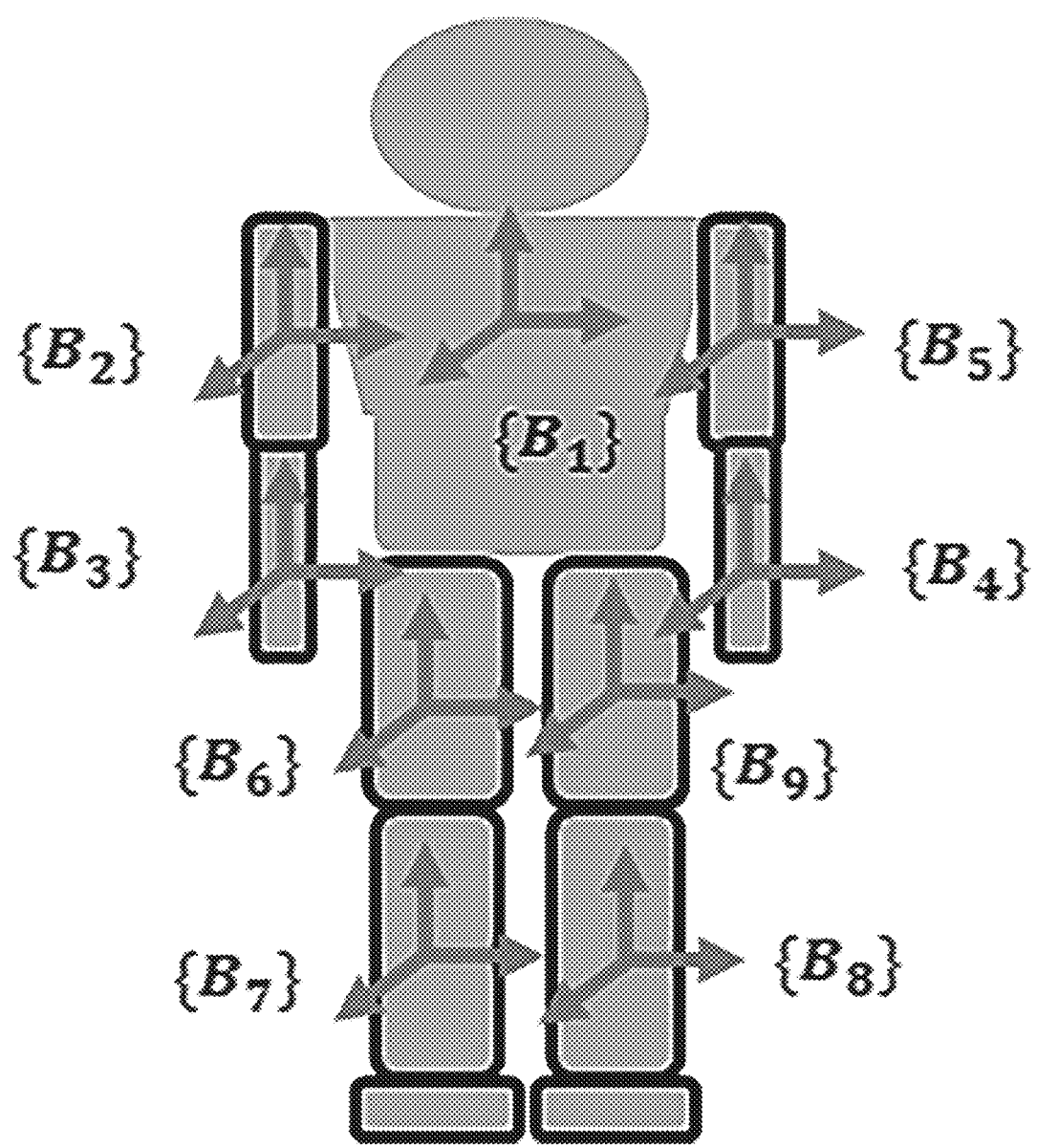
FIG. 4 is a diagram for describing a body coordinate system according to an embodiment of the present disclosure.

FIG. 4 is a diagram for describing the body coordinate system according to an embodiment of the present disclosure.

Referring to FIG. 4, the body coordinate systems {B1, B2, . . . , B9} of the body segments having the plurality of motion sensors attached thereto, i.e., the upper arms, the lower arms, the thighs and the calves on the left/right sides may be each set (S100).

Referring back to FIG. 3, the calibration method includes: the step (S200) of calculating a first rotation matrix $N_k$ of each motion sensor by acquiring the outputs of the plurality of motion sensors in a first basic pose of the subject. Here, k denotes the index of the motion sensor.

When vectors in the direction of gravity and Earth's magnetic field are referred to as g and m respectively, the world coordinate system {W} is assumed in which $-g$ direction is represented as one axis (for example, y axis) of the world frame, and $(-g \times m)$ is represented as the other axis (for example, x axis). Then, the output of the motion sensor is a rotation matrix of a sensor coordinate system of the motion sensor on the basis of the world coordinate system. That is, sensor data of the motion sensor indicates the rotation matrix from the world coordinate system to the sensor coordinate system of the motion sensor.

The sensor coordinate system for each motion sensor attached to the subject may be different from the body coordinate system of the corresponding body segment. Accordingly, to calculate the ratio of body size or capture the motion, a correlation between the sensor coordinate system and the body coordinate system is required. The process of calculating the correlation between the sensor coordinate system and the body coordinate system will be described in more detail in the following steps S200 to S400.

In the step S200, when the outputs of the plurality of motion sensors in the first basic pose of the subject are acquired, the first rotation matrix $N_k$ from the world coordinate system to the sensor coordinate system of each motion sensor is each calculated.

Figure 5:
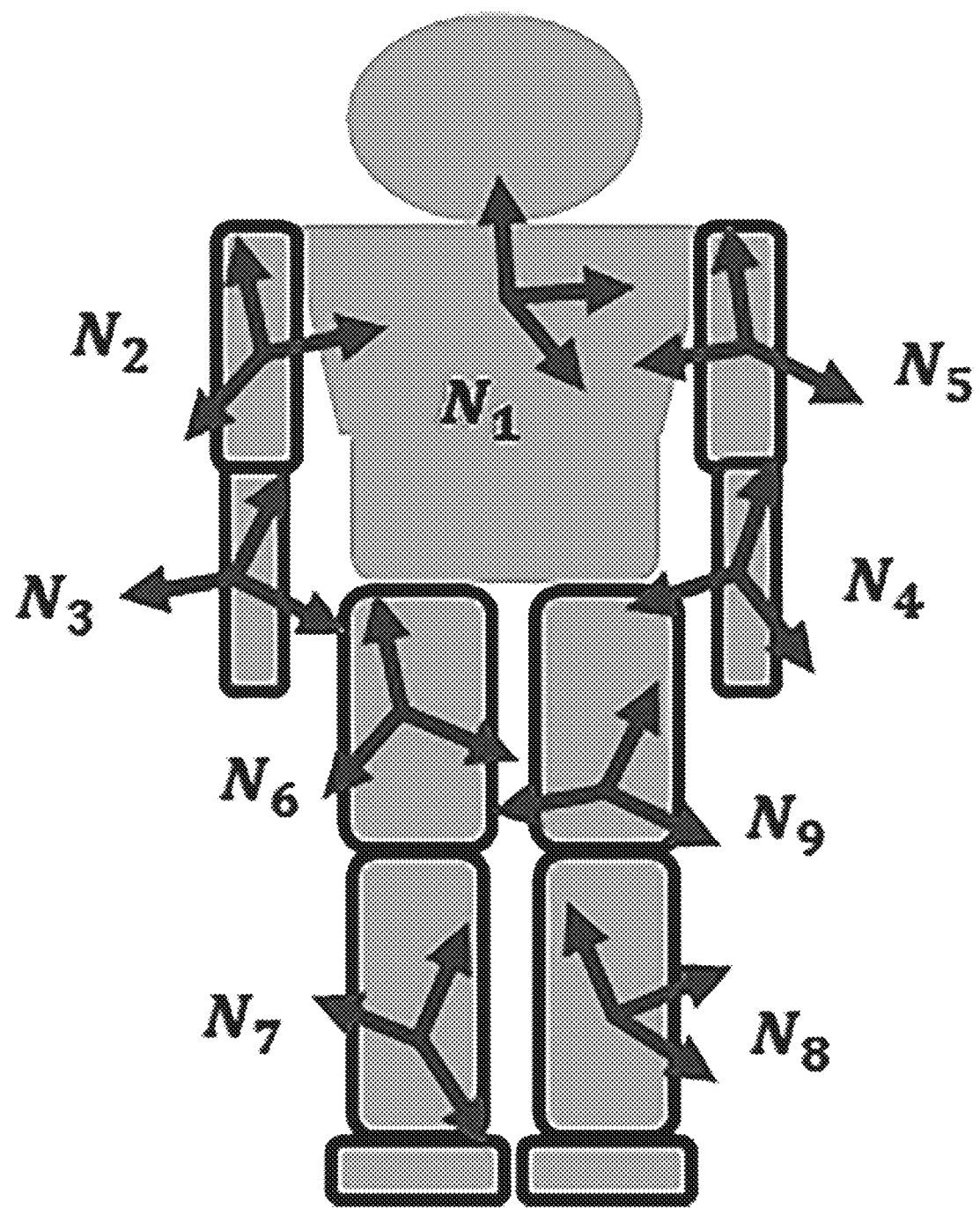
FIG. 5 is a diagram for describing a process of calculating a first rotation matrix $N_k$ of each motion sensor in a first basic pose according to an embodiment of the present disclosure.

FIG. 5 is a diagram for describing the process of calculating the first rotation matrix $N_k$ of each motion sensor in the first basic pose according to an embodiment of the present disclosure.

Referring to FIG. 5, the first basic pose may be a standing pose at which the rotatable body segment is positioned toward the direction of the ground. The first basic pose may be referred to as "standing at attention".

In an embodiment, the first rotation matrix $N_k$ from the world coordinate system to the sensor coordinate system of the respective motion sensor may be calculated based on multiple outputs. In this case, the step S200 may include: the step (S210) of acquiring the output of the motion sensor in the first basic pose of the subject; the step (S220) of repeating the step S210 n times (where n is an integer of 2 or greater); and the step (S230) of calculating an average of n outputs acquired through the step S220. Then, the average of the multiple outputs is used in the steps S300 to S500 as the first rotation matrix $N_k$ from the world coordinate system to the sensor coordinate system for each motion sensor.

Referring back to FIG. 3, the calibration method includes: the step (S300) of calculating a second rotation matrix $T_k$ of each motion sensor by acquiring the outputs of the plurality of motion sensors in a second basic pose of the subject.

When the outputs of the plurality of motion sensors in the second basic pose of the subject are acquired in the step S200, the second rotation matrix $T_k$ from the world coordinate system to the sensor coordinate system of each motion sensor is each calculated in the step S300.

Figure 6A:
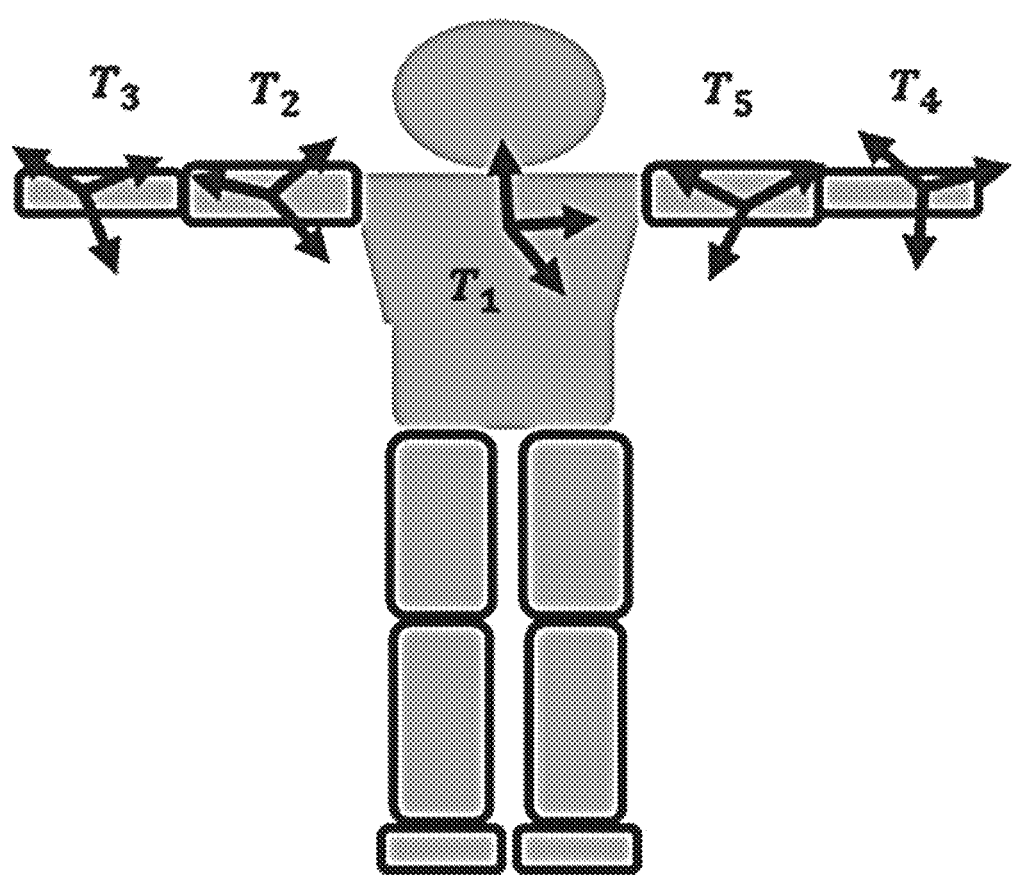
FIGS. 6A to 6C are diagrams for describing a process of calculating a second rotation matrix $T_k$ of each motion sensor in a second basic pose according to an embodiment of the present disclosure.
Figure 6B:
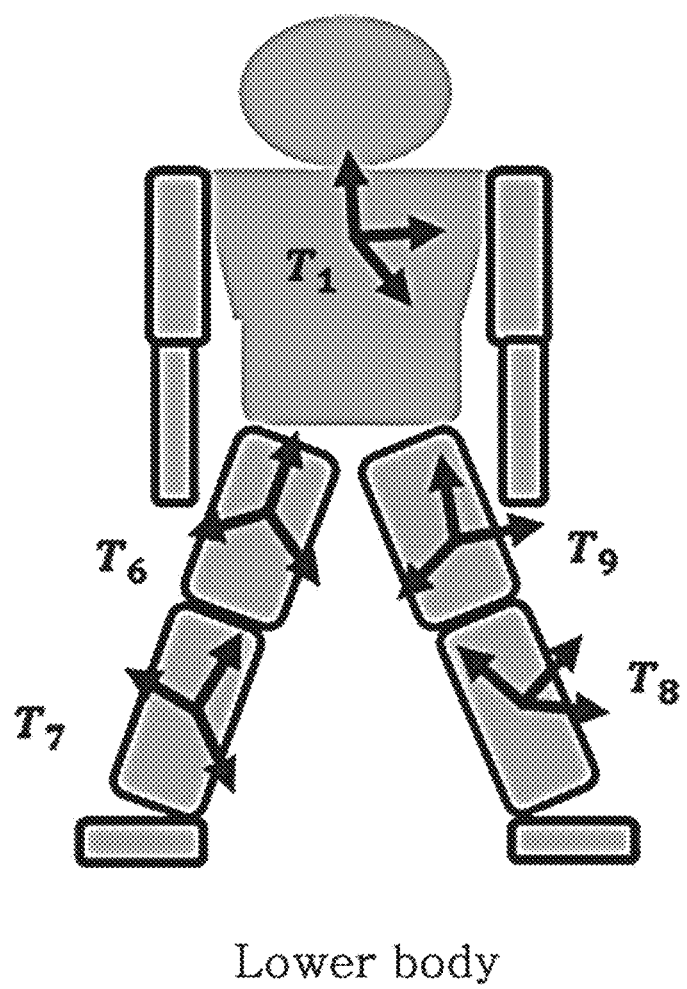
Figure 6C:
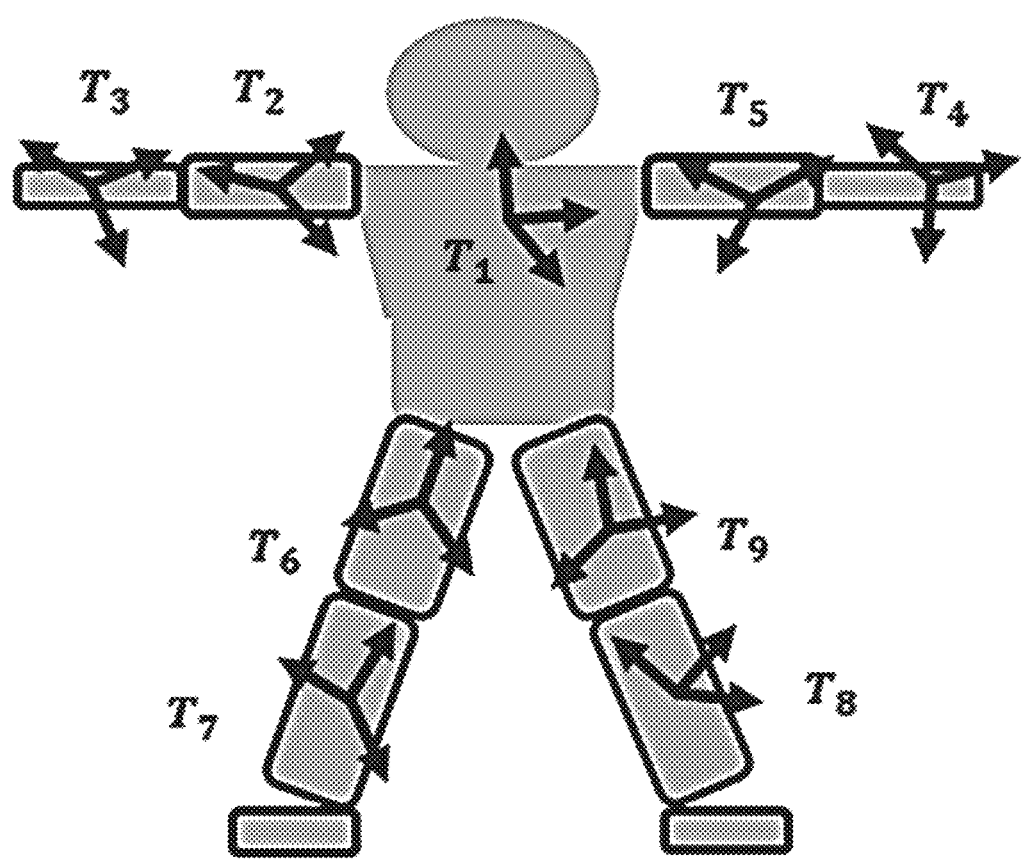

FIGS. 6A to 6C are diagrams for describing the process of calculating the second rotation matrix $T_k$ of each motion sensor in the second basic pose according to an embodiment of the present disclosure.

Referring to FIGS. 6A to 6C, the second basic pose may be a pose in which some or all of the rotatable body segments are moved to the sides on the basis of the first basic pose, and then paused. In an embodiment, the second basic pose may be a pose in which the body segments included in the upper body and the body segments included in the lower body among the rotatable body segments and a combination thereof are moved to the sides.

In an example, the second basic pose may be a pose in which the rotatable body segments included in the upper body, i.e., the arms are stretched to the sides as shown in FIG. 6A.

In another example, the second basic pose may be a pose in which the rotatable body segments included in the lower body, i.e., the legs are spread wide apart as shown in FIG. 6B.

In still another example, the second basic pose may be the combination pose of FIGS. 6A and 6B, i.e., the arms stretched to the sides at the upper body and both legs spread apart at the lower body.

In an embodiment, the second rotation matrix $T_k$ from the world coordinate system to the sensor coordinate system of the respective motion sensor may be calculated based on multiple outputs. In this case, the step S300 may include: the step (S310) of acquiring the output of the motion sensor in the second basic pose of the subject; the step (S320) of repeating the step S310 n times (where n is an integer of 2 or greater); and the step (S330) of calculating an average of n outputs acquired through the step S320. Then, the average of the multiple outputs is used in the steps S300 to S500 as the second rotation matrix $T_k$ from the world coordinate system to the sensor coordinate system for each motion sensor.

Referring back to FIG. 3, the calibration method includes: the step (S400) of calculating a rotation matrix A from the world coordinate system to the body coordinate system of the trunk having the first motion sensor attached thereto for the first motion sensor attached to the trunk. In the specification, the rotation matrix A is referred to as a third rotation matrix to distinguish it from the first and second rotation matrices.

To calculate a ratio of body size, a correlation between the body coordinate system and the sensor coordinate system is required. As the correlation between the world coordinate system and the sensor coordinate system is calculated in the steps S100 and S200, a correlation between the world coordinate system and the body coordinate system is required.

In an embodiment, the step S400 may include: the step (S410) of setting a first unit vector v1 based on the direction of gravity; the step (S420) of calculating a second unit vector v2 based on the first and second rotation matrices; the step (S430) of calculating a third unit vector based on the first and second unit vectors v1, v2; and the step (S440) of acquiring the third rotation matrix A from the world coordinate system to the body coordinate system of the trunk having the first motion sensor attached thereto.

In the step S410, the first unit vector v1 may be set to {0, 0, 1}.

In an embodiment, the second unit vector v2 may be represented by the following Equation 1.

$$v_2 \triangleq e/\|e\| \quad \text{[Equation 1]}$$

Here, e is represented by the following Equation 2.

$$e \triangleq (a_1, a_2, a_3) \quad \text{[Equation 2]}$$

Here, a1, a2, a3 are calculated by the following Equation 3.

$$E - E^T \triangleq \begin{bmatrix} 0 & -a_3 & a_2 \\ a_3 & 0 & -a_1 \\ -a_2 & a_1 & 0 \end{bmatrix} \quad \text{[Equation 3]}$$

Here, E is an average matrix of $N_k^{-1} T_k$ (k=2, ..., n). $E^T$ is a transpose matrix of the matrix E. Since the trunk does not move in the first basic pose and the second basic pose, the first rotation matrix $N_1$ and the second rotation matrix $T_1$ of the first motion sensor attached to the trunk are equal. Accordingly, the first rotation matrix $N_1$ and the second rotation matrix $T_1$ of the first motion sensor may not be used to calculate the average matrix E.

In the step S440, the third rotation matrix A from the world coordinate system to the body coordinate system of the trunk having the first motion sensor attached thereto is given as the following Equation 4 {first unit vector, second unit vector, third unit vector}.

$$A \triangleq [\, v_1 \quad v_2 \quad v_3 \,] \quad \text{[Equation 4]}$$

The third rotation matrix A corresponds to the body coordinate system {B1} of the trunk. When the body coordinate system {B1} of the trunk is set as shown in FIG. 3, v1 may denote the head direction, v2 may denote the front direction, and v3 may denote the side direction.

The correlation between the world coordinate system and the body coordinate system is acquired by acquiring the rotation matrix A of the body coordinate system based on the world coordinate system in the step S400. Thus, the correlation between the body coordinate system and the sensor coordinate system may be acquired, and finally the sensor coordinate system {N1} of the first motion sensor may be calculated based on the body coordinate system {B1} of the trunk having the first motion sensor attached thereto.

Referring back to FIG. 3, the calibration method includes: the step (S500) of calculating a ratio of body size of the subject based on the outputs of the plurality of motion sensors and the third rotation matrix.

The body size of the subject may include: the size of the rotatable body segment; the size of the upper body including the trunk; the size of the lower body and/or the size of the full body including the upper body and the lower body. The size of the trunk includes the length of the vertical direction (for example, the vertical length) and/or the length of the horizontal direction (for example, the horizontal length). The face is excluded from the full body.

In an embodiment, the step S500 may include: the step (S510) of acquiring the outputs of the plurality of motion sensors while the subject is moving arbitrarily; the step (S520) of setting a motion unit vector for at least some of the plurality of motion sensors; and the step (S530) of calculating a ratio of at least some of the plurality of body segments in the motion pose of the subject based on the motion unit vector. In the step S530, ratios of various body sizes are calculated based on the motion unit vector.

In the step S510, sensor data outputted from the plurality of motion sensors attached to the subject is acquired. The sensor data may be subset into outputs for each motion sensor. The output for each motion sensor includes the sensing results of the corresponding attached body segment at the sensing timestamp.

In the step S510, the output of the motion sensor, i.e., the sensor data is acquired while the subject is moving arbitrarily. Here, the arbitrary motion includes various motions, and may or may not include a motion of taking a specific pose as shown in FIGS. 4 to 6.

The output of the motion sensor acquired in the step S510 indicates a rotation matrix from the world coordinate system to the sensor coordinate system of the corresponding motion sensor. To distinguish it from the first rotation matrix $N_k$ and the second rotation matrix $T_k$, the output of the motion sensor in the step S510 or the rotation matrix indicated thereby is referred to as $U_k$.

Figure 7:
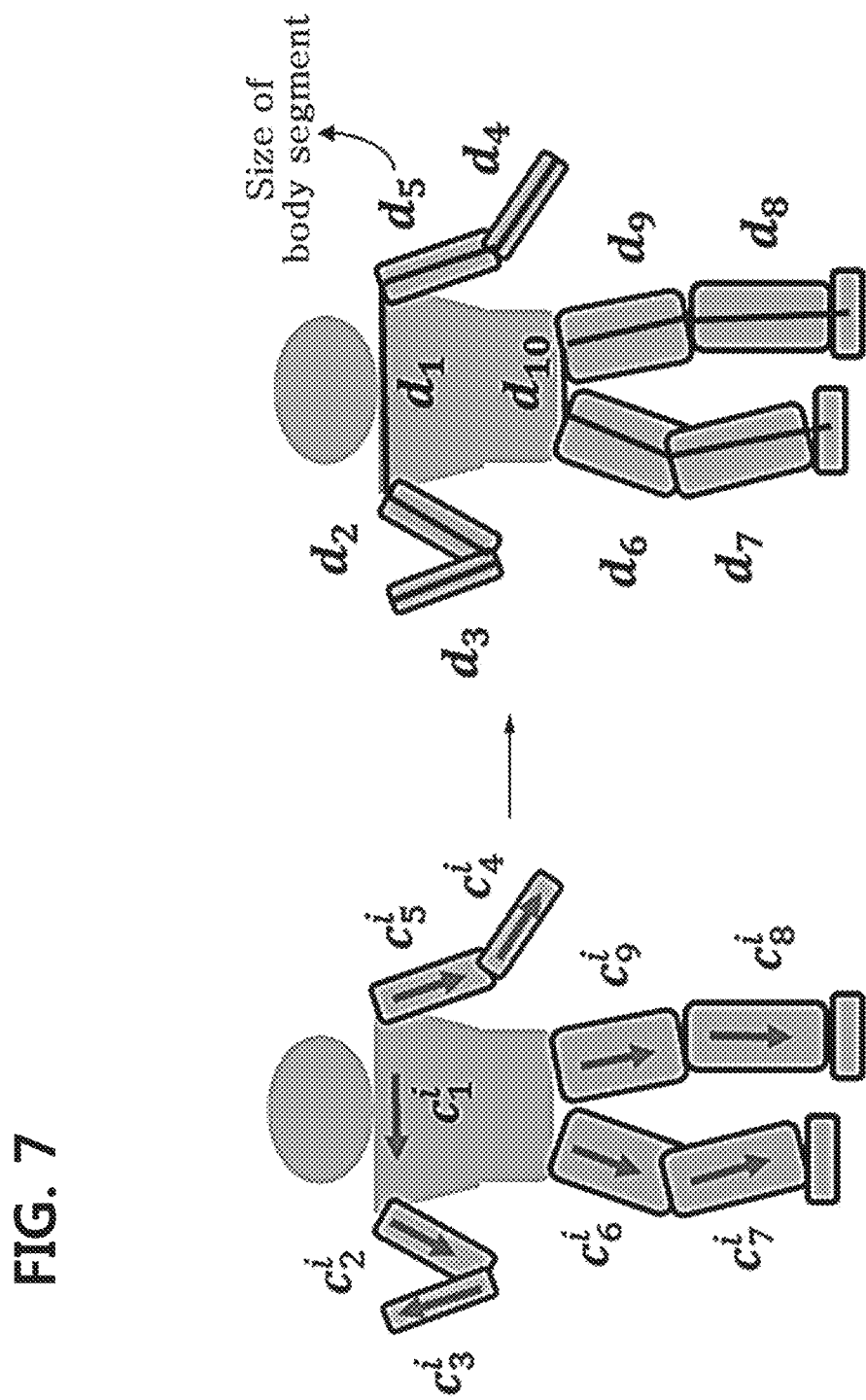
FIG. 7 is a diagram for describing a motion unit vector and the size of body segment according to an embodiment of the present disclosure.

FIG. 7 is a diagram for describing the motion unit vector and the size of the body segment according to an embodiment of the present disclosure.

Referring to FIG. 7, in the step S520, the motion unit vector is set for each motion sensor. The motion unit vector is set for each of the body segments having the plurality of motion sensors attached thereto.

In an embodiment, the motion unit vector $c_1^i$ of the first motion sensor attached to the trunk among the plurality of motion sensors is set in the horizontal direction of the trunk. The calibration system may pre-store the definition of the motion unit vector $c_1^i$ for the first motion sensor attached to for the trunk, and when the first motion sensor attached to the trunk is a 3-axis sensor, may set sensor data of the horizontal direction of the trunk among 3-axis sensor data as the motion unit vector $c_1^i$.

In the step S520, the motion unit vector (for example, $c_2^i, \ldots, c_n^i$) except the first motion sensor may be set in a direction in which the body segment having the motion sensor attached thereto extends from the trunk.

Then, as shown in FIG. 7, a ratio of size of the specific body segment having the motion sensor attached thereto may be calculated using the motion unit vector corresponding to the motion sensor (S530).

In the n motion sensors, the motion unit vector of n-1 motion sensors is set by the following Equation 5.

$$c_k^i \triangleq -R_k^i v_1 \ (k = 2, \ldots, n) \qquad \text{[Equation 5]}$$

Here, $c_k$ denotes the motion unit vector of the $k^{th}$ motion sensor, i denotes the sensing timestamp, and v1 is the first unit vector set based on the direction of gravity. In the embodiments of FIG. 7, n is 9.

The $R_k$ is represented by the following Equation 6.

$$R_k^i \triangleq A^{-1} U_k^i \qquad \text{[Equation 6]}$$

Here, A denotes the third rotation matrix from the world coordinate system to the sensor coordinate system of the first motion sensor. $U_k$ indicates the output of the motion sensor in an arbitrary motion. The $U_k$ is the output of the corresponding motion sensor, and the output of the motion sensor in the corresponding motion indicates the rotation matrix from the world coordinate system to the sensor coordinate system of the motion sensor.

In the step S520, the motion unit vector ($c_k^i$, k=2, ..., 9) of the second to ninth motion sensors of FIG. 7 is set by the representation of the above Equation 5.

Ratios of various body sizes including a ratio of the size of the body segment having each motion sensor attached thereto, a ratio of upper body size, a ratio of lower body size and/or a ratio of the full body size are calculated based on the motion unit vector set in the step S520 (S530).

In an embodiment, the step (S530) includes: acquiring the outputs of the plurality of motion sensors in a first closed loop pose of the subject, and calculating a ratio of sizes of body segments that form a first closed loop based on the outputs.

Figure 8:
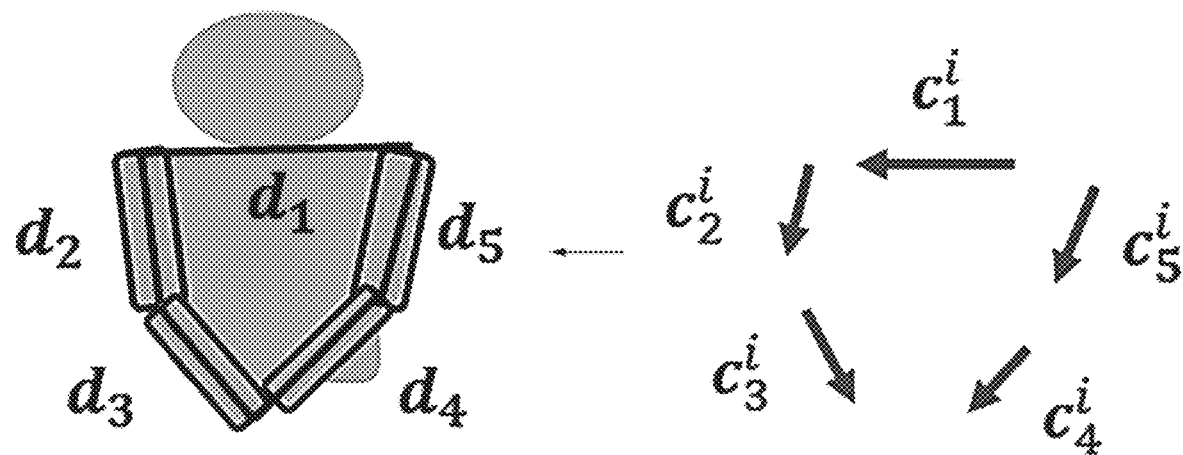
FIG. 8 is a diagram showing a subject in a first closed loop pose according to an embodiment of the present disclosure.

FIG. 8 is a diagram showing the subject in the first closed loop pose according to an embodiment of the present disclosure.

Referring to FIG. 8, the first closed loop pose is a pose in which body segments belonging to the upper body of the subject form a closed loop.

Here, the body segments that belong to the upper body and form the first closed loop include the top part of the trunk and the left/right arms (the upper arm and the lower arm). The top part of the trunk is the body segment above the waist, and for example, may be between the shoulders as shown in FIGS. 7 and 8.

In the first closed loop pose, the remaining body segments except the body segments that form the closed loop may have an arbitrary movement. Additionally, the first closed loop pose includes a pose in which the body segments that form the closed loop move while maintaining the closed loop.

In an example, as shown in FIG. 8, the first closed loop may be formed by the contact between both arms extending from the top part of the trunk. Then, a ratio of body segment sizes (for example, d2, d3, d4, d5 in FIG. 8) of both arms that form the first closed loop is calculated (S530).

In detail, when the outputs of the plurality of motion sensors are acquired while the subject is moving arbitrarily in the first closed loop pose (S510), the motion unit vector in the first closed loop condition is set through the above Equations 4 and 5 (S520). Here, the set motion unit vector includes the motion unit vector $c_1^i$ for the trunk, and the motion unit vectors $c_2^i, c_3^i, c_4^i, c_5^i$ for the upper arms and the lower arms on the left/right sides, which form the first closed loop. In the specification, the motion unit vector set based on the outputs of the plurality of motion sensors in the first closed loop condition may be referred to as the motion unit vector in the first closed loop condition.

The motion unit vectors $c_1^i, c_2^i, c_3^i, c_4^i, c_5^i$ of the first closed loop are calculated through the above-described Equations 4 and 5. Then, a ratio of the sizes $d_1, d_2, d_3, d_4, d_5$ of the body segments that form the first closed loop is calculated based on the motion unit vector in the first closed loop condition (S530).

In the above example, a ratio of sizes of the upper arms and the lower arms on the left/right sides and/or the trunk that form the first closed loop is calculated (S530). Here, as the calculated ratio of the size of the trunk is the length of the loop direction, it is a ratio of the horizontal length (d1 in FIG. 8) of the trunk.

In an embodiment, the ratio of the sizes of the body segments that form the first closed loop may be calculated by the following Equation 7.

$$\min_{x \in \mathbb{R}^5} \sum_{i=1}^{m} \|F_i x\|^2 \quad \text{[Equation 7]}$$

where, $x = (x_1, \ldots, x_5) \in \mathbb{R}^5$ and $\|x\| = 1$ $$F_i \triangleq [\, c_1^i \quad c_2^i \quad c_3^i \quad -c_4^i \quad -c_5^i \,] \in \mathbb{R}^{3 \times 5}$$

In the above Equation 7, m is the time range in which sensor data is acquired. A variable value at $i^{th}$ sensing timestamp acquired between first to $m^{th}$ is applied to the above Equation 7.

In the above Equation 7, x is a set of ratios of the sizes of the body segments that form the first closed loop. For example, in FIG. 8, a ratio x1 of the horizontal length of the trunk and ratios x2, x3, x4, x5 of the sizes of the upper arms and the sizes of the lower arms which form the first closed loop are components of the set x. As the component x1 in the set x represents a ratio of the size $d_k$ of the body segment (body link), a value of x is positive. The sum of ratios should satisfy 1.

In the above Equation 7, Fi is a matrix including the motion unit vectors of the motion sensors each attached to the body segments that form the first closed loop. In the embodiment of FIG. 8, since the first closed loop includes the trunk and both arms, Fi includes first to fifth motion unit vectors corresponding to the corresponding body segments. In the Fi, the sign of the motion unit vector relies on the loop forming direction and the setting direction of the motion unit vector. Since the setting direction and the loop direction of the fourth and fifth motion unit vectors are opposite to each other, in the Fi, the negative sign is allocated to the fourth and fifth motion unit vectors.

The ratio of the sizes of the body segments that form the first closed loop is calculated by the above Equation 7 (S530).

The body segment size $d_k$ is $\alpha \|c_k\|$ (k is the index of the body segment). A solution to the linear optimization problem with the above Equation 7 may be calculated using m measurement values detected under the first closed loop condition. Then, the component value of x satisfying the condition of the above Equation 7 is calculated. As the components x1, x2, x3, x4, x5 of the x indicate the ratios of the sizes of the body segments, finally the ratio of the sizes of the body segments that form the first closed loop is each calculated through the linear optimization solution with the above Equation 7.

In an embodiment, the first closed loop may be formed with a symmetrical structure.

Figure 9:
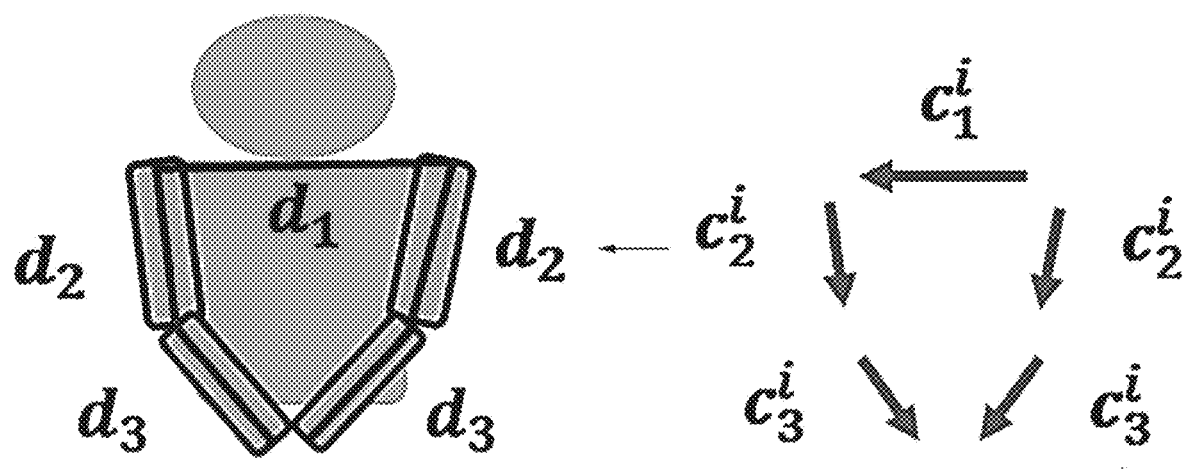
FIG. 9 is a diagram showing a subject in a symmetrical first closed loop pose according to an embodiment of the present disclosure.

FIG. 9 is a diagram showing the subject in the symmetrical first closed loop pose according to an embodiment of the present disclosure.

As shown in FIG. 9, in the first closed loop, a second body segment having the second motion sensor attached thereto and a fifth body segment having the fifth motion sensor attached thereto may have a symmetrical structure, and a third body segment having the third motion sensor attached thereto and a fourth body segment having the fourth motion sensor attached thereto may have a symmetrical structure.

As such, when the first closed loop is formed in symmetry, the ratio of the sizes of the body segments (i.e., including the trunk and both arms) that form the first closed loop is calculated based on Equation 8 having modification to the components corresponding to the symmetry in Equation 7 (S530). As the fourth and fifth motion sensors are symmetrical to the second and third motion sensors, the indices corresponding to the fourth and fifth motion sensors are replaced.

$$\min_{x \in \mathbb{R}^3} \sum_{i=1}^{m} \|G_i x\|^2 \quad \text{[Equation 8]}$$

where, $x = (x_1, \ldots, x_3) \in \mathbb{R}^5$ and $\|x\| = 1$ $$G_i \triangleq [\, c_1^i \quad (c_2^i - c_5^i) \quad (c_3^i - c_4^i) \,] \in \mathbb{R}^{3 \times 3}$$

Through the above Equation 8, a ratio of sizes of body segments of the subject that forms the first closed loop in which the upper body is in symmetry may be calculated. Due to the symmetrical relationship, a ratio of sizes of all five body segments that form the first closed loop may be acquired by calculating a ratio of sizes of three body segments.

In an embodiment, the step S530 includes: acquiring the outputs of the plurality of motion sensors in a second closed loop pose of the subject, and calculating a ratio of sizes of body segments that form the second closed loop based on the outputs.

Figure 10:
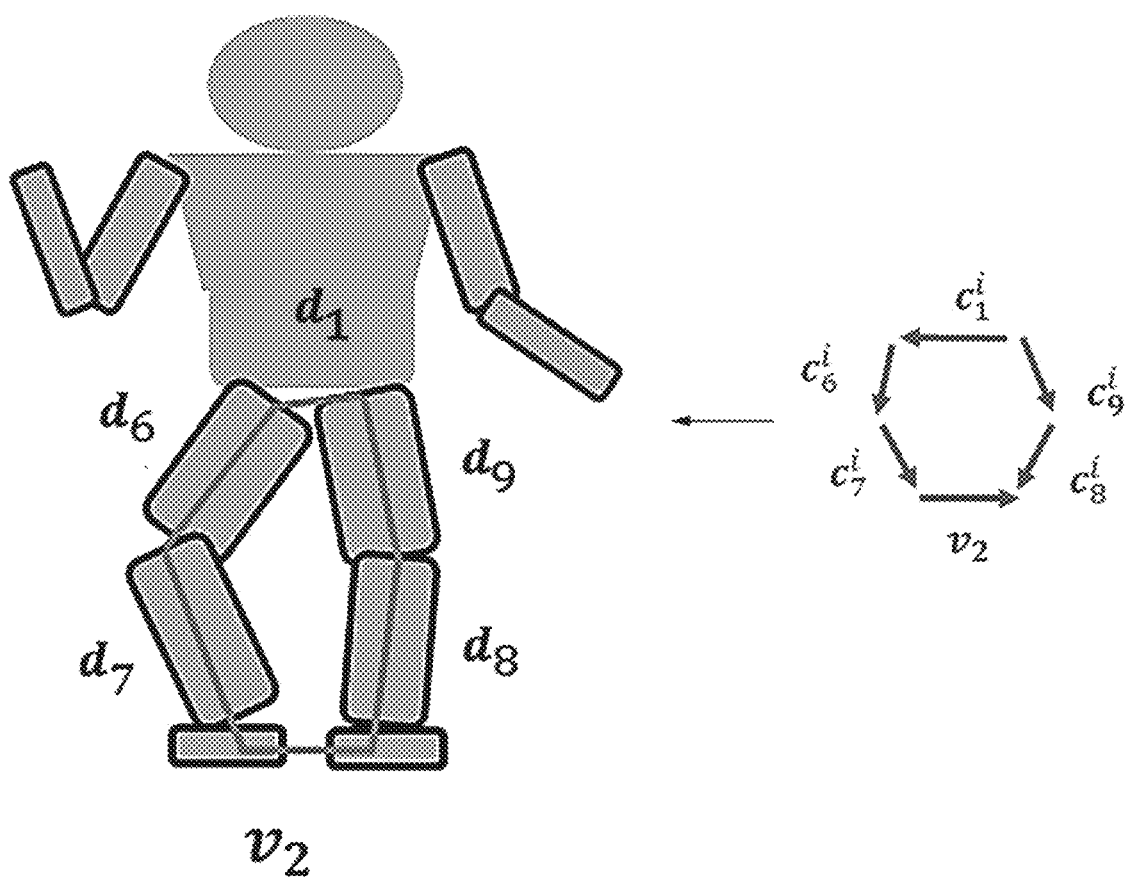
FIG. 10 is a diagram showing a subject in a second closed loop pose according to an embodiment of the present disclosure.

FIG. 10 is a diagram showing the subject in the second closed loop pose according to an embodiment of the present disclosure.

Referring to FIG. 10, the second closed loop pose is a pose in which body segments belonging to the lower body of the subject form a closed loop.

Here, the body segments that belong to the lower body and form the second closed loop include the bottom part of the trunk and left/right legs (thighs and calves). The bottom part of the trunk may be, for example, the waist as shown in FIG. 10. In specific embodiments, the size of the bottom part of the trunk and the size of the top part of the trunk are all the horizontal length (d1 in FIG. 10) of the trunk and may be treated as the same value.

In the second closed loop pose, the remaining body segments except the body segments forming the closed loop may have an arbitrary movement. Additionally, the second closed loop pose includes a pose in which the body segments forming the closed loop moves while maintaining the closed loop.

In an example, as shown in FIG. 10, both legs extending from the bottom part of the trunk may come into contact with the ground. Then, a ratio of sizes of both legs (for example, d6, d7, d8, d9 in FIG. 10) forming the second closed loop is calculated (S530).

In detail, when the outputs of the plurality of motion sensors are acquired while the subject is freely arbitrarily moving the other body segments forming the second closed loop (S510), the motion unit vector in the second closed loop condition is calculated through the above Equations 4 and 5 (S520).

The motion unit vector includes the motion unit vector $c_1^i$ of the trunk and the motion unit vectors $c_6^i, c_7^i, c_8^i, c_9^i$ of the left/right calves and thighs, which form the second closed loop. Additionally, the motion unit vector may further include a vector v2 between the legs (S520). The vector v2 is acquired based on the output while in motion with the feet fixed on the ground in the step S510 (S520).

In the specification, the motion unit vector set based on the outputs of the plurality of motion sensors in the second closed loop condition may be referred to as the motion unit vector in the second closed loop condition.

The ratio of sizes of body segments that form the second closed loop is calculated based on the motion unit vector in the second closed loop condition (S530).

In the above example, the ratio of the sizes of the left/right calves and thighs, and/or the trunk that form the second closed loop is calculated (S530). Here, the calculated ratio of the size of the trunk is the length of the loop direction, and is a ratio of the horizontal length (d1 in FIG. 10) of the trunk.

In an embodiment, the ratio x of the sizes $d_1, d_6, d_7, d_8, d_9$ of the body segments that form the second closed loop may be calculated by the following Equation 9.

$$\min_{x \in \mathbb{R}^6} \sum_{i=1}^{m} \|H_i x\|^2 \qquad \text{[Equation 9]}$$

where, $x = (x_1, \ldots, x_6) \in \mathbb{R}^6$ and $\|x\| = 1$ $$H_i \triangleq \begin{bmatrix} c_1^i & c_6^i & c_7^i & v_2 & -c_8^i & -c_9^i \end{bmatrix} \in \mathbb{R}^{3 \times 6}$$

Similar to the embodiment of FIG. 7, the ratio of the sizes $d_1, d_6, d_7, d_8, d_9$ of the body segments that form the second closed loop is each calculated through the linear optimization solution for the above Equation 9. x1, x2, x3, x4 and x5 among the components of the set x represent that the set x includes five components. That is, it will be obvious to those skilled in the art that compared to Equation 7, only the index is the same, but even the body segment (or size) is not the same.

Figure 11:
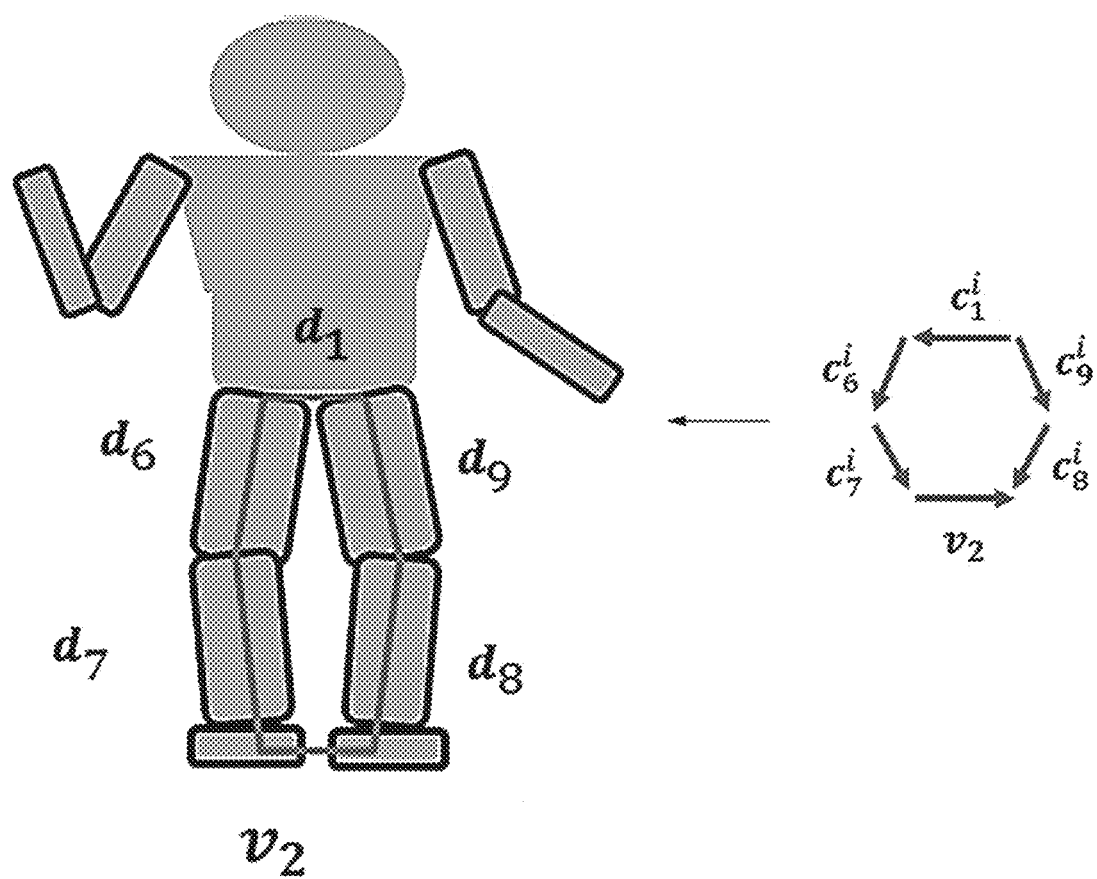
FIG. 11 is a diagram showing a subject in a symmetrical second closed loop pose according to an embodiment of the present disclosure.

FIG. 11 is a diagram showing the subject in the symmetrical second closed loop pose according to an embodiment of the present disclosure.

As shown in FIG. 11, in the second closed loop, a sixth body segment having the sixth motion sensor attached thereto and a ninth body segment having the ninth motion sensor attached thereto may have a symmetrical structure, and a seventh body segment having the seventh motion sensor attached thereto and an eighth body segment having the eighth motion sensor attached thereto may have a symmetrical structure.

As such, when the second closed loop is formed in symmetry, the ratio of the sizes of the body segments (i.e., including the trunk and the legs) that form the second closed loop is calculated based on Equation 10 having modification to the components corresponding to the symmetry in Equation 9 (S530).

The symmetrical relationship in the closed loop condition has been described with reference to FIGS. 8 and 9, and a detailed description is omitted herein.

Meanwhile, as described above, in Equations 7 to 9, the motion unit vector $c_1$ is used to calculate the ratio of the size of the trunk. The ratio of the size of the trunk calculated using the motion unit vector $c_1$ is a ratio of the size of the body segment extending the motion unit vector $c_1$, and for example, a ratio of the horizontal length d1 of the trunk. To calculate the size of the upper body, the vertical length h of the trunk is required.

In an embodiment, the step S530 includes: calculating a ratio of the vertical length of the trunk.

The ratio of the vertical length of the trunk is calculated based on the output of the motion sensor acquired in a third closed loop condition formed by one arm and the trunk, or a fourth closed loop condition formed by one arm and one thigh and the trunk.

Figure 12:
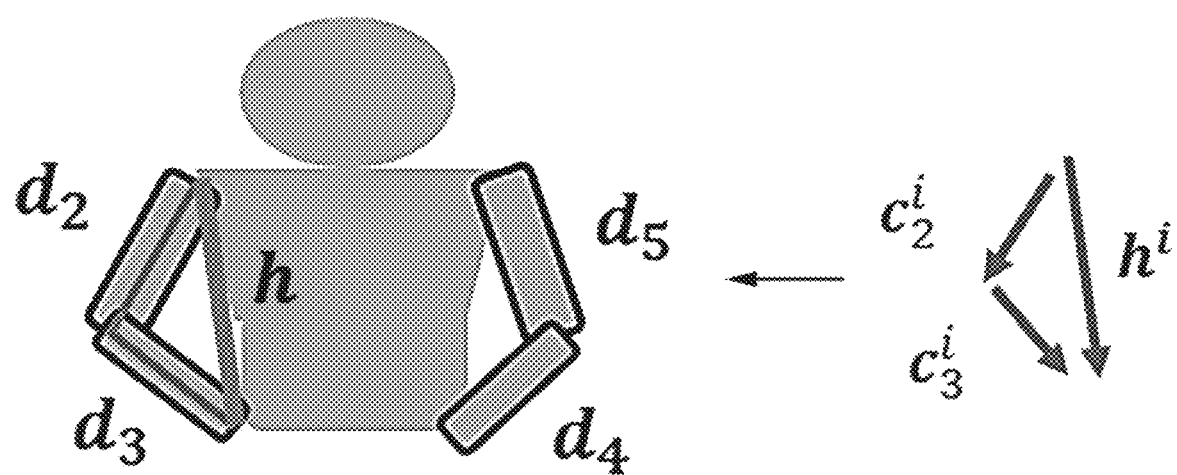
FIG. 12 is a diagram showing a subject in a third closed loop pose according to an embodiment of the present disclosure.

FIG. 12 is a diagram showing the subject in the third closed loop pose according to an embodiment of the present disclosure.

Referring to FIG. 12, the third closed loop pose is a pose in which the arm and the trunk of the subject form a closed loop. While the subject is moving arbitrarily when the subject forms the third closed loop by the arm and the trunk, the output of the motion sensor is acquired (S510). The output of the motion sensor includes sensor data of the motion sensor attached to the arm and the trunk that form the third closed loop.

The motion unit vector that forms the third closed loop is represented based on the output of the motion sensor in the third closed loop pose (S520). When the outputs of the plurality of motion sensors in the third closed loop pose are acquired (S510), the motion unit vectors $c_2, c_3$, h in the third closed loop condition are set through the above Equations 4 and 5 (S520).

The ratio of the sizes of the body segments that form the third closed loop including the vertical length of the trunk is calculated based on the motion unit vectors (S530). The ratio x of the sizes $d_2, d_3$, h of the body segments that form the third closed loop is calculated through the following Equation 10.

$$\min_{x \in \mathbb{R}^3} \sum_{i=1}^{m} \|I_i x\|^2 \qquad \text{[Equation 10]}$$

where, $x = (x_1, \ldots, x_3) \in \mathbb{R}^3$ and $\|x\| = 1$ $$I_i \triangleq \begin{bmatrix} c_2^i & c_3^i & -h^i \end{bmatrix} \in \mathbb{R}^{3 \times 3}$$

Similar to the embodiment of FIG. 7, the ratio of the sizes $d_2, d_3$, h of the body segments that form the third closed loop is each calculated through the linear optimization solution for the above Equation 10. x1, x2, x3 among the components of the set x represent that the set x includes three components. That is, it will be obvious to those skilled in the art that compared to Equation 7, only the index is the same, but even the body segment (or size) is not the same.

Figure 13:
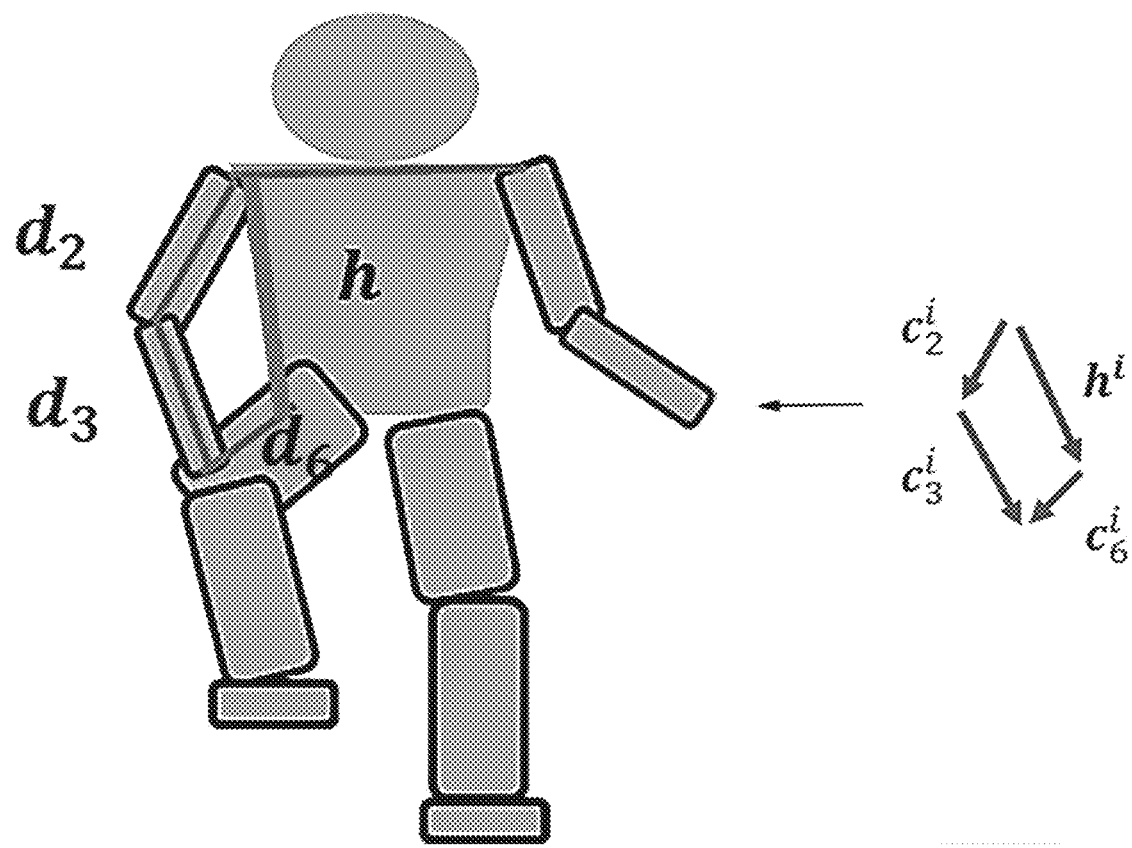
FIG. 13 is a diagram showing a subject in a fourth closed loop pose according to another embodiment of the present disclosure.

FIG. 13 is a diagram showing the subject in the fourth closed loop pose according to another embodiment of the present disclosure.

Referring to FIG. 13, the fourth closed loop pose is a pose in which at least parts of the trunk, the arm and the leg of the subject form a fourth closed loop. For example, the fourth closed loop is formed by the trunk h, the upper/lower arms $d_2$, $d_3$ and the thigh $d_6$ of the subject. While the subject is moving arbitrarily when the fourth closed loop is formed by the arms, the trunk and the thigh of the subject, the output of the motion sensor is acquired (S510). The output of the motion sensor includes sensor data of the motion sensors attached to the arms, the trunk and the thigh that form the fourth closed loop.

The motion unit vector that forms the fourth closed loop is represented based on the output of the motion sensor in the fourth closed loop (S520). When the outputs of the plurality of motion sensors are acquired (S510), the motion unit vectors $c_2$, $c_3$, $c_6$, h in the fourth closed loop condition are set through the above Equations 4 and 5 (S520).

The ratio of the sizes of the body segments that form the fourth closed loop including the vertical length of the trunk is calculated based on the motion unit vectors (S530). The ratio x of the sizes $d_2$, $d_3$, $d_6$, h of the body segments that form the fourth closed loop is calculated through the following Equation 11.

$$\min_{x \in \mathbb{R}^4} \sum_{i=1}^{m} \|J_i x\|^2 \quad \text{[Equation 11]}$$

where, $x = (x_1, \ldots, x_4) \in \mathbb{R}^4$ and $\|x\| = 1$ $$J_i \triangleq \begin{bmatrix} c_2^i & c_3^i & -c_6^i & -h^i \end{bmatrix} \in \mathbb{R}^{3 \times 4}$$

Similar to the embodiment of FIG. 7, the ratio of the sizes $d_2$, $d_3$, $d_6$, h of the body segments that form the fourth closed loop is each calculated through the linear optimization solution for the above Equation 11. x1, x2, x3, x4 among the components of the set x represent that the set x includes four components. That is, it will be obvious to those skilled in the art that compared to Equation 7, only the index is the same, but even the body segment (or size) is not the same.

As such, the calibration system 1 may calculate the ratio of body size of the target subject for motion capture only using the motion sensor originally required for motion capture without a separate device.

It will be obvious to those skilled in the art that the calibration system 1 or some components may include other components not described herein. For example, the calibration system 1 may include other hardware elements necessary for the operation described herein, including a network interface, an input device for data entry, a display, an output device for printing or displaying other data and memory that stores data.

The operation by the system 1 and method for calibrating a ratio of body size of the subject according to the embodiments as described above may be, at least in part, implemented in a computer program and recorded in a computer-readable recording medium. For example, it may be implemented with a program product on the computer-readable medium including program code, and may be executed by the processor for performing any or all of the above-described steps, operations or processes.

The computer may be a computing device such as a desktop computer, a laptop computer, a notebook computer, a smart phone or like, and may be any integrated device. The computer is a device having at least one alternative and specialized processor, memory, storage, and networking component (either wireless or wired). The computer may run an operating system (OS) such as, for example, OS that is compatible with Microsoft Windows, Apple OS X or iOS, Linux distribution, or Google Android OS.

The computer-readable recording medium includes all types of recording and identification devices in which computer-readable data is stored. Examples of the computer-readable recording medium include read only memory (ROM), random access memory (RAM), compact disc read only memory (CD-ROM), magnetic tape, floppy disk, and optical data storage and identification devices. Additionally, the computer-readable recording medium is distributed over computer systems connected via a network, and may store and execute the computer-readable code in a distributed manner. Additionally, a functional program, code and a code segment for realizing this embodiment will be easily understood by persons having ordinary skill in the technical field to which this embodiment belongs.

While the present disclosure has been hereinabove described with reference to the embodiments shown in the drawings, this is provided by way of illustration and those skilled in the art will understand that various modifications and variations may be made thereto. However, it should be understood that such modifications fall within the scope of technical protection of the present disclosure. Accordingly, the true technical protection scope of the present disclosure should be defined by the technical spirit of the appended claims.

The invention claimed is:

1. A method for calibrating a ratio of body size of a subject, the method comprising:
   setting a body coordinate system of each body segment in a subject having a plurality of motion sensors attached to a plurality of body segments;
   calculating a first rotation matrix from a world coordinate system set based on the ground to a sensor coordinate system of each motion sensor when the subject takes a first basic pose;
   calculating a second rotation matrix from the world coordinate system to the sensor coordinate system of each motion sensor when the subject takes a second basic pose;
   calculating a third rotation matrix from the world coordinate system to the body coordinate system of a trunk having a first motion sensor attached thereto for the first motion sensor attached to the trunk of the subject;
   calculating a ratio of body size of the subject based on outputs of the plurality of motion sensors and the third rotation matrix; and
   capturing motion information of the subject based on the calculating the ratio of body size of the subject based on the outputs of the plurality of motion sensors and the third rotation matrix;
   wherein calculating the third rotation matrix from the world coordinate system to the body coordinate system of the trunk having the first motion sensor attached thereto for the first motion sensor attached to the trunk of the subject comprises:
   setting a first unit vector based on a direction of gravity;
   setting a second unit vector based on the first and second rotation matrices;

setting a third unit vector based on the first and second unit vectors; and acquiring the third rotation matrix from the world coordinate system to the body coordinate system of the trunk having the first motion sensor attached thereto, wherein the third rotation matrix is given as the following Equation 1:

$$A \triangleq [\begin{array}{ccc} v_1 & v_2 & v_3 \end{array}].$$ [Equation 1]

2. The method according to claim 1, wherein the first basic pose is a pose in which an arm or a leg of the subject is positioned toward the ground, and the second basic pose is a pose in which at least one of the arm or the leg is moved to a side from the first basic pose.

3. The method according to claim 1, wherein the second unit vector is represented by the following Equation 2:

$$v_2 \triangleq e/\|e\|$$ [Equation 2]

where v2 is the second unit vector, and e is represented by the following Equation 3:

$$e \triangleq (a_1, a_2, a_3)$$ [Equation 3]

where a1, a2, a3 are calculated by the following Equation 4, $$E - E^T \triangleq \begin{bmatrix} 0 & -a_3 & a_2 \\ a_3 & 0 & -a_1 \\ -a_2 & a_1 & 0 \end{bmatrix}$$ [Equation 4]

where E denotes an average matrix of $N_k^{-1}T_k$ (where k=2, ..., n), $N_k$ denotes the first rotation matrix, $T_k$ denotes the second rotation matrix, and n denotes the number of the remaining motion sensors except the first motion sensor attached to the trunk among the plurality of motion sensors.

4. The method according to claim 1, wherein calculating the ratio of body size of the subject comprises:

acquiring the outputs of the plurality of motion sensors while the subject is moving arbitrarily;

setting a motion unit vector for each of the plurality of motion sensors; and calculating a ratio of at least some of the plurality of body segments in a motion pose taken by the subject based on the motion unit vector.

5. The method according to claim 4, wherein the motion unit vector of the first motion sensor attached to the trunk among the plurality of motion sensors is set in a horizontal direction of the trunk, and the motion unit vector of the remaining motion sensors in the plurality of motion sensors is set by the following Equation 5:

$$c_k^i \triangleq -R_k^i v_1 (k = 2, \ldots, n)$$ [Equation 5]

where ck denotes the motion unit vector of $k^{th}$ motion sensor, i denotes a sensing timestamp, v1 denotes the first unit vector set based on the direction of gravity, and $R_k$ is represented by the following Equation 6:

$$R_k^i \triangleq A^{-1} U_k^i$$ [Equation 6]

where A denotes the third rotation matrix, and $U_k$ denotes the output of the corresponding motion sensor.

6. The method according to claim 5, wherein calculating the ratio of at least some of the plurality of body segments in the motion pose taken by the subject based on the motion unit vector comprises:

calculating a ratio of sizes of body segments that form a first closed loop, wherein the body segments that form the first closed loop include the trunk and both arms, and the ratio of the sizes of the body segments that form the first closed loop is calculated by the following Equation 7:

$$\min_{x \in \mathbb{R}^5} \sum_{i=1}^{m} \|F_i x\|^2$$ [Equation 7]

where, $x = (x_1, \ldots, x_5) \in \mathbb{R}^5$ and $\|x\| = 1$ $$F_i \triangleq [\begin{array}{ccccc} c_1^i & c_2^i & c_3^i & -c_4^i & -c_5^i \end{array}] \in \mathbb{R}^{3 \times 5}$$

where x is a set of ratios of the body segments that form the first closed loop, and m is a time range in which the outputs of the plurality of motion sensors are acquired.

7. The method according to claim 6, wherein when the first closed loop is symmetrical, the ratio of the sizes of the body segments that form the first closed loop is calculated by the following Equation 8, and $$\min_{x \in \mathbb{R}^3} \sum_{i=1}^{m} \|G_i x\|^2$$ [Equation 8]

where, $x = (x_1, \ldots, x_3) \in \mathbb{R}^5$ and $\|x\| = 1$ $$G_i \triangleq [\begin{array}{ccc} c_1^i & (c_2^i - c_5^i) & (c_3^i - c_4^i) \end{array}] \in \mathbb{R}^{3 \times 3}$$

the symmetrical first closed loop is such that a second body segment having the second motion sensor attached thereto and a fifth body segment having the fifth motion sensor attached thereto are symmetrical, and a third body segment having the third motion sensor attached thereto and a fourth body segment having the fourth motion sensor attached thereto are symmetrical.

8. The method according to claim 5, wherein calculating the ratio of at least some of the plurality of body segments in the motion pose taken by the subject based on the motion unit vector comprises:

calculating a ratio of sizes of body segments that form a second closed loop, wherein the body segments that form the second closed loop include the trunk and both legs, and the ratio of the sizes of the body segments that form the second closed loop is calculated by the following Equation 9:

$$\min_{x \in \mathbb{R}^6} \sum_{i=1}^{m} \|H_i x\|^2 \qquad \text{[Equation 9]}$$

where, $x = (x_1, \ldots, x_6) \in \mathbb{R}^6$ and $\|x\| = 1$ $$H_i \triangleq [\, c_1^i \ c_6^i \ c_7^i \ v_2 \ -c_8^i \ -c_9^i \,] \in \mathbb{R}^{3 \times 6}$$

where x is a set of ratios of the body segments that form the second closed loop, and m is a time range in which the outputs of the plurality of motion sensors are acquired.

9. The method according to claim 5, wherein calculating the ratio of at least some of the plurality of body segments in the motion pose taken by the subject based on the motion unit vector comprises:

calculating a ratio of sizes of body segments that form a third closed loop, wherein the body segments that form the third closed loop include one arm and the trunk, and the calculated ratio of the size of the trunk indicates a ratio of a vertical length of the trunk, and the ratio of the sizes of the body segments that form the third closed loop is calculated by the following Equation 10:

$$\min_{x \in \mathbb{R}^3} \sum_{i=1}^{m} \|I_i x\|^2 \qquad \text{[Equation 10]}$$

where, $x = (x_1, \ldots, x_3) \in \mathbb{R}^3$ and $\|x\| = 1$ $$I_i \triangleq [\, c_2^i \ c_3^i \ -h^i \,] \in \mathbb{R}^{3 \times 3}$$

where x is a set of ratios of the body segments that form the third closed loop, and m is a time range in which the outputs of the plurality of motion sensors are acquired.

10. The method according to claim 5, wherein calculating the ratio of at least some of the plurality of body segments in the motion pose taken by the subject based on the motion unit vector comprises:

calculating a ratio of sizes of body segments that form a fourth closed loop, wherein the body segments that form the fourth closed loop include one arm, the trunk and one thigh, and the calculated ratio of the size of the trunk indicates a ratio of a vertical length of the trunk, and the ratio of the sizes of the body segments that form the fourth closed loop is calculated by the following Equation 11:

$$\min_{x \in \mathbb{R}^4} \sum_{i=i}^{m} \|J_i x\|^2 \qquad \text{[Equation 11]}$$

where, $x = (x_1, \ldots, x_4) \in \mathbb{R}^4$ and $\|x\| = 1$ $$J_i \triangleq [\, c_2^i \ c_3^i \ -c_6^i \ -h^i \,] \in \mathbb{R}^{3 \times 4}$$

where x is a set of ratios of the body segments that form the fourth closed loop, and m is a time range in which the outputs of the plurality of motion sensors are acquired.

11. A non-transitory computer-readable recording medium having recorded thereon a program including instructions for performing the method for calibrating a ratio of body size of a subject according to claim 1.

12. A system for calibrating a ratio of body size of a subject, the system comprising:

a plurality of motion sensors attached to a plurality of body segments of the subject; and a data processing device to acquire outputs of the plurality of motion sensors and calibrate a ratio of body size of the subject, wherein the data processing device is configured to:

set a body coordinate system of each body segment in the subject, calculate a first rotation matrix from a world coordinate system set based on the ground to a sensor coordinate system of each motion sensor when the subject takes a first basic pose, calculate a second rotation matrix from the world coordinate system to the sensor coordinate system of each motion sensor when the subject takes a second basic pose, calculate a third rotation matrix from the world coordinate system to the body coordinate system of a trunk for a first motion sensor attached to the trunk of the subject, calculate a ratio of body size of the subject based on the outputs of the plurality of motion sensors and the third rotation matrix, and capture motion information of the subject based on the calculating the ratio of body size of the subject based on the outputs of the plurality of motion sensors and the third rotation matrix, wherein to calculate the third rotation matrix from the world coordinate system to the body coordinate system of the trunk having the first motion sensor attached thereto for the first motion sensor attached to the trunk of the subject, the data processing device is further configured to:

set a first unit vector based on a direction of gravity, set a second unit vector based on the first and second rotation matrices, set a third unit vector based on the first and second unit vectors, and acquire the third rotation matrix from the world coordinate system to the body coordinate system of the trunk having the first motion sensor attached thereto, wherein the third rotation matrix is given as the following Equation 1:

$$A \triangleq [\, v_1 \ v_2 \ v_3 \,]. \qquad \text{[Equation 1]}$$

\* \* \* \* \*